United States Patent
Zhang

(10) Patent No.: US 8,827,885 B2
(45) Date of Patent: Sep. 9, 2014

(54) METHOD FOR IMPLEMENTING LOW-FREQUENCY ROTATING CONSTANT HIGH MAGNETIC FIELD

(75) Inventor: Gongbi Zhang, Guangdong (CN)

(73) Assignee: Shenzhen Heng an Hong Yuan Mag-Tech Co., Ltd., Shenzhen (CN)

( * ) Notice: Subject to any disclaimer, the term of this patent is extended or adjusted under 35 U.S.C. 154(b) by 177 days.

(21) Appl. No.: 13/497,128

(22) PCT Filed: Jul. 6, 2009

(86) PCT No.: PCT/CN2009/072638
§ 371 (c)(1),
(2), (4) Date: Mar. 20, 2012

(87) PCT Pub. No.: WO2011/003230
PCT Pub. Date: Jan. 13, 2011

(65) Prior Publication Data
US 2012/0238797 A1    Sep. 20, 2012

(51) Int. Cl.
*A61N 2/00* (2006.01)
*A61N 2/06* (2006.01)
*A61N 2/08* (2006.01)
*A61N 2/12* (2006.01)
*H01F 7/02* (2006.01)

(52) U.S. Cl.
CPC ............... *A61N 2/12* (2013.01); *H01F 7/0294* (2013.01)
USPC .......................................................... 600/9

(58) Field of Classification Search
CPC ............ A61N 2/00; A61N 2/06; A61N 2/08; A61N 2/12
USPC .................................................. 600/9; 601/15
See application file for complete search history.

(56) References Cited

U.S. PATENT DOCUMENTS

| 4,537,141 A | 8/1985 | Brunner | |
| 5,667,469 A * | 9/1997 | Zhang et al. | 600/9 |
| 2008/0230459 A1 * | 9/2008 | Donahue et al. | 210/222 |
| 2009/0091411 A1 * | 4/2009 | Zhang et al. | 335/306 |

FOREIGN PATENT DOCUMENTS

| CN | 86206534 | 12/1987 |
| CN | 2038026 | 5/1989 |
| CN | 1101585 | 4/1995 |
| CN | 1208660 | 2/1999 |
| CN | 1208660 A * | 2/1999 |
| CN | 1339326 | 3/2002 |
| CN | 1583193 | 2/2005 |
| CN | 2824987 | 10/2006 |

* cited by examiner

*Primary Examiner* — Charles A Marmor, II
*Assistant Examiner* — Thaddeus Cox
(74) *Attorney, Agent, or Firm* — Hamre, Schumann, Mueller & Larson, P.C.

(57) ABSTRACT

A method for implementing a low-frequency rotating constant high magnetic field is disclosed. The method includes disposing an even number of more than two high field magnets, and disposing a magnetically permeable rotating arm. The high field magnets are symmetrically and fixedly mounted on the same surface of the magnetically permeable rotating arm. Magnetic poles of free surfaces of two symmetrical high field magnets are opposite. The area of the free surface of the high field magnet is larger than that of a connecting surface. A cross section of the high field magnet is in a geometric shape without edges or corners. A rotating apparatus drives the magnetically permeable rotating arm and the high field magnets to rotate.

8 Claims, 5 Drawing Sheets

METHOD FOR IMPLEMENTING LOW-FREQUENCY ROTATING CONSTANT HIGH MAGNETIC FIELD

BACKGROUND

1. Technical Field

The present invention relates to a method for implementing magnetic therapy, and more particularly to a method for implementing a low-frequency rotating constant high magnetic field.

2. Related Art

The magnetic field has an obvious influence on human body and other creatures, as well as water or chemical agents. In view of this, the magnetic field is applied to human body for local high magnetic field therapy, which is referred to as magnetic therapy. The magnetic therapy is not new in modern medicine, and magnetic therapy instruments are common, for example, Chinese Patent (Application No. 88214746.4) entitled "Electric Magnetic Therapy Apparatus", Chinese Patent (Application No. 86206534) entitled "Magnetic Rotator for Medical Treatment", and U.S. patent (U.S. Pat. No. 4,537,141) entitled "Magnetic Apparatus for Non-surgically Eliminating Calcium Deposit in Human Body". However, all of the above patents have defects, and in view of the defects, the applicant has provided a high magnetic field therapy apparatus, referring to the invention patent (Patent No. 93114013,1) entitled "High Magnetic Field Therapeutic Apparatus Using Low-frequency Rotating Permanent Magnet" which was applied by the applicant previously. The magnetic therapy instruments in the above patents, including the magnetic therapy instrument in the patent applied by the applicant, and other magnetic therapy instruments currently available on the market all adopt an open magnetic field for magnetic therapy. The open magnetic field has intrinsic defects. In one aspect, the open magnetic field inevitably causes leakage of magnetic lines of force, and the leaked magnetic lines of force fail to contribute to the magnetic therapy and are wasted. In addition, the leakage of the magnetic lines of force affects adjacent devices, for example, mobile phones, televisions and radios. In another aspect, the magnetic lines of force of the open magnetic field are scattered, the intensity of the magnetic field is low, and the penetration distance of the magnetic lines of force is short, leading to an undesirable magnetic therapy effect.

SUMMARY

In view of the defects in the prior art that the magnetic therapy instruments adopt an open magnetic field, which easily causes leakage of magnetic lines of force and leads to an undesirable magnetic therapy effect, the present invention provides a method for implementing a low-frequency rotating constant high magnetic field. The method adopts an even number of high field magnets, in which the high field magnets are fixedly mounted on a magnetically permeable rotating arm, a cross section of the high field magnet is in a geometric shape without edges or corners, thereby greatly reducing the leakage of magnetic lines of force around the high field magnet and the amount of magnets. The area of a connecting surface of the high field magnet connected to the magnetically permeable rotating arm is smaller than that of a free surface symmetrical to the connecting surface, thereby ensuring that magnetic lines of force emerge from a free surface of one high field magnet and returns from a free surface of another high field magnet. As the magnetic lines of force inside the magnet enter from one magnet to another magnet through the magnetically permeable rotating arm, no leakage occurs, so that the magnetic lines of force are concentrated, and maximum magnetic field intensity is achieved. A rotating apparatus is used to drive the magnetically permeable rotating arm and the high field magnets to rotate, thereby achieving the objective of low-frequency high magnetic field therapy.

The technical solution adopted in the present invention to solve the technical problem is to provide a method for implementing a low-frequency rotating constant high magnetic field. The method includes disposing an even number of more than two high field magnets, and disposing a magnetically permeable rotating arm, in which the high field magnets are symmetrically and fixedly mounted on the same surface of the magnetically permeable rotating arm, magnetic poles of free surfaces of two symmetrical high field magnets are opposite, the area of the free surface of the high field magnet is larger than that of a connecting surface, a cross section of the high field magnet is in a geometric shape without edges or corners, and an rotating apparatus drives the magnetically permeable rotating arm and the high field magnets to rotate.

The technical solution adopted in the present invention to solve the technical problem further includes the following.

The cross section of the high field magnet is in a shape of a circle or an ellipse.

The high field magnet is a taper or a cone.

The high field magnet is a taper with an ellipse-shaped cross section, a cone with an ellipse-shaped cross section, or a hemisphere with an ellipse-shaped cross section.

The high field magnet is a taper with a circle-shaped cross section, a cone with a circle-shaped cross section, or a hemisphere with a circle-shaped cross section.

The number of the high field magnets is two.

The material of the magnetically permeable rotating arm is a high magnetic permeability material.

The rotating apparatus is an electrical motor, a mounting hole is opened on the rotating arm, an electrical motor shaft is inserted in the mounting hole, and a key connection is adopted between the electrical motor shaft and the rotating arm.

The beneficial effect of the present invention is that, the present invention adopts the high field magnet of a special shape as a magnetic therapy apparatus, in which the cross section of the high field magnet has no edge or corner, which reduces the magnetic leakage around the magnet, so that the magnet lines of force are concentrated and emerge upward, thereby reducing magnetic leakage in other directions, increasing the intensity of the magnetic field in a useful direction, effectively preventing interference on other electrical appliances, and greatly reducing the amount of magnets. The present invention adopts the conical magnet, and the area of an upward surface (that is, the free surface) is larger than that of a downward surface (that is, the connecting surface), so that according to an edge effect of the magnetic field, the upward emerging height of the magnetic lines of force is greater, and the magnetic flux density is greater, thereby achieving a better magnetic therapy effect.

The present invention is further illustrated below through specific embodiments with reference to the accompanying drawings

BRIEF DESCRIPTION OF THE DRAWINGS

The present disclosure will become more fully understood from the detailed description given herein below for illustration only, and thus are not limitative of the present disclosure, and wherein.

The meanings of the serial numbers are as follows: 1—high field magnet, 2—magnetically permeable rotating arm, 3—fixing plate, 4—electrical motor, 5—electrical motor shaft, 6—key, 7—mounting hole, 8—backrest, 9—base, 10—adjusting lever, 11—bearing plate, 12—up-down electrical motor, 13—guide block, 14—lead screw, 15—longitudinal guide rod, 16—guide magnet, 17—action magnet, 18—traverse guide rod, 19—slide block.

DETAILED DESCRIPTION

This embodiment is a preferred embodiment of the present invention, and all other embodiments having principles or basic structures the same as or similar to this embodiment shall fall within the protection scope of the present invention.

Figure 1:
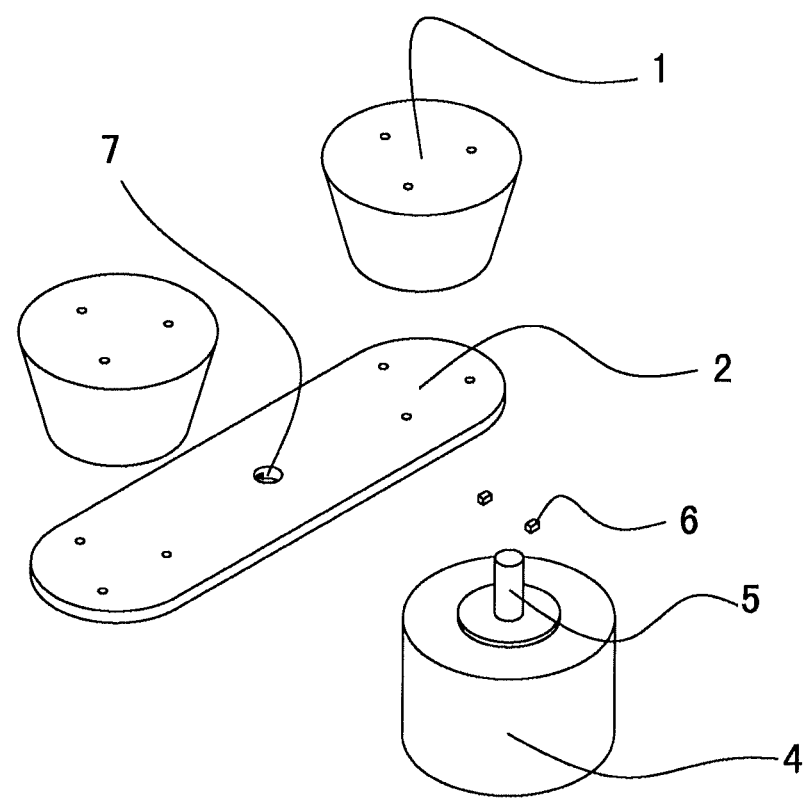
FIG. 1 is a schematic structural view of an exploded state of Embodiment 1 of the present invention.
Figure 2:
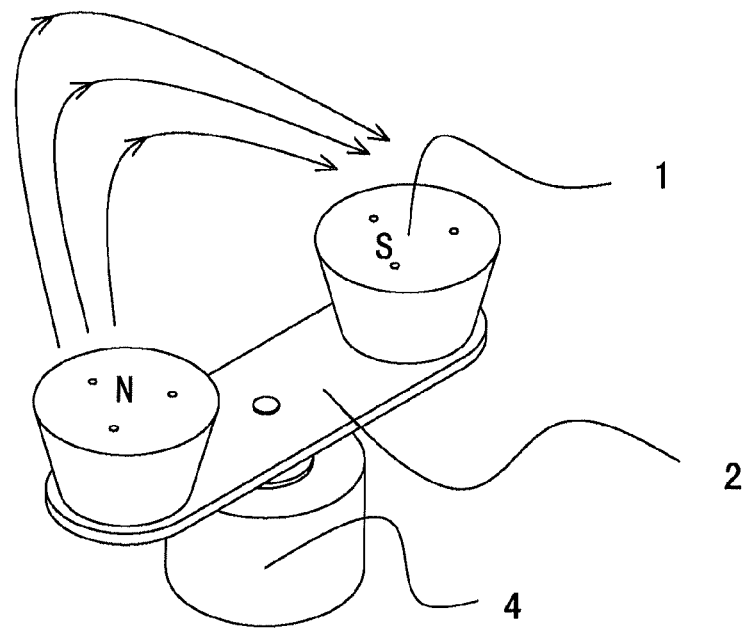
FIG. 2 is a three-dimensional schematic structural view of Embodiment 1 of the present invention.

Embodiment 1: Referring to FIG. 1 and FIG. 2, the present invention mainly includes high field magnets 1, a magnetically permeable rotating arm 2 and a rotating electrical motor 4. In this embodiment, the magnetically permeable rotating arm 2 is made of an A3 steel plate, and during specific implementation, other magnetically permeable materials may also be adopted. The magnetically permeable rotating arm 2 is elongated, having two ends respectively fixedly mounted with one high field magnet 1. In this embodiment, the high field magnet 1 is in a shape of a cone. In this embodiment, a smaller surface (that is, a lower surface) of the high field magnet 1 is fixedly mounted on the magnetically permeable rotating arm 2, and is defined as a connecting surface of the magnet 1. A larger surface (that is, an upper surface) of the high field magnet 1 is a high magnetic field action surface, and is defined as a free surface of the magnet 1. In this embodiment, the high field magnet 1 is fixedly mounted on the magnetically permeable rotating arm 2 through a screw, and during specific implementation, other connection manners may also be adopted. A mounting hole 7 is opened in the middle of the magnetically permeable rotating arm 2. An electrical motor shaft 5 of an electrical motor 4 is inserted in the mounting hole 7. The electrical motor shaft 5 and the magnetically permeable rotating arm 2 are connected through a key 6. The electrical motor 4 is used to drive the magnetically permeable rotating arm 2 and the high field magnets 1 on the magnetically permeable rotating arm 2 to rotate at a low frequency.

Figure 3:
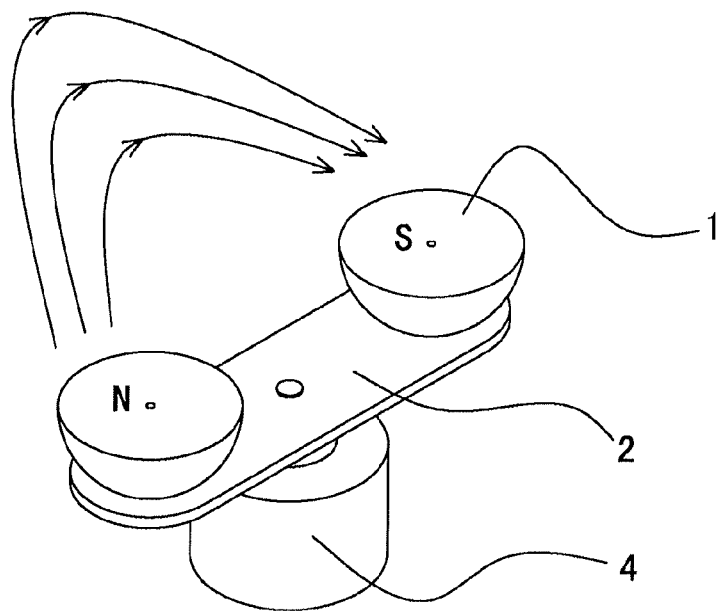
FIG. 3 is a three-dimensional schematic structural view of Embodiment 2 of the present invention.

Embodiment 2: Referring to FIG. 3, this embodiment also includes high field magnets 1, a magnetically permeable rotating arm 2 and an electrical motor 4. In this embodiment, the high field magnet 1 is in a shape of a hemisphere. A lower surface (that is, a point on a spherical crown corresponding to a center of circle of a bottom surface) of the high field magnet 1 is fixedly mounted on the magnetically permeable rotating arm 2, and an upper surface (that is, a bottom plane) of the high field magnet 1 is a high magnetic field action surface. In this embodiment, the high field magnet 1 is fixedly mounted on the magnetically permeable rotating arm 2 through a screw, and during specific implementation, other connection manners may also be adopted. In this embodiment, the electrical motor 4 is also used to drive the magnetically permeable rotating arm 2 and the high field magnets 1 on the magnetically permeable rotating arm 2 to rotate at a low frequency.

Figure 4:
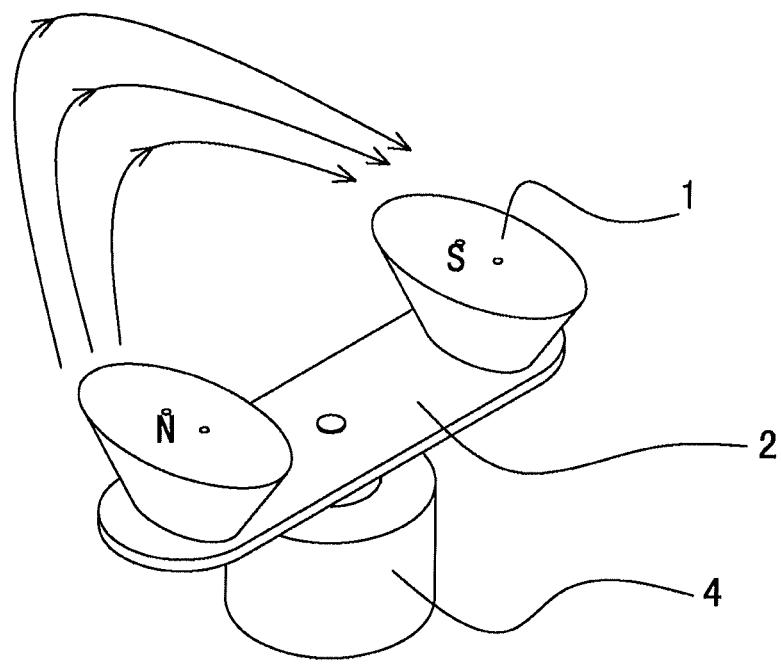
FIG. 4 is a three-dimensional schematic structural view of Embodiment 3 of the present invention.

Embodiment 3: Referring to FIG. 4, this embodiment also includes high field magnets 1, a magnetically permeable rotating arm 2 and an electrical motor 4. In this embodiment, the high field magnet 1 is in a shape of a cone. A cross section of the high field magnet 1 is in a shape of an ellipse. A lower surface (that is, a smaller surface) of the high field magnet 1 is fixedly mounted on the magnetically permeable rotating arm 2, and an upper surface (that is, a larger surface) of the high field magnet 1 is a high magnetic field action surface. In this embodiment, the high field magnet 1 is fixedly mounted on the magnetically permeable rotating arm 2 through a screw, and during specific implementation, other connection manners may also be adopted. In this embodiment, the rotating electrical motor 4 is also used to drive the magnetically permeable rotating arm 2 and the high field magnets 1 on the magnetically permeable rotating arm 2 to rotate at a low frequency.

Figure 5:
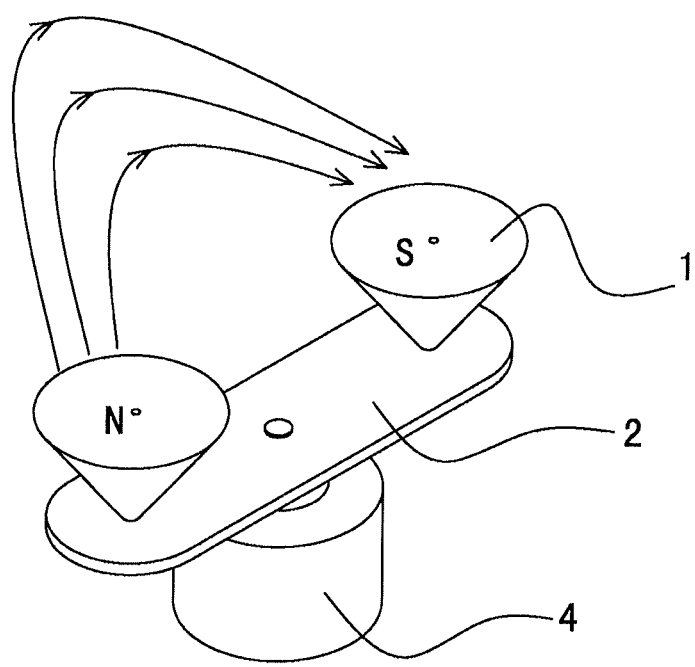
FIG. 5 is a three-dimensional schematic structural view of Embodiment 4 of the present invention.

Embodiment 4: Referring to FIG. 5, this embodiment also includes high field magnets 1, a magnetically permeable rotating arm 2 and an electrical motor 4. In this embodiment, the high field magnet 1 is in a shape of a taper. A lower surface (or more specifically, the vertex of the taper) of the high field magnet 1 is fixedly mounted on the magnetically permeable rotating arm 2 (the vertex of the taper is inserted in the magnetically permeable rotating arm 2), and an upper surface (that is, a bottom plane) of the high field magnet 1 is a high magnetic field action surface. In this embodiment, the high field magnet 1 is fixedly mounted on the magnet permeable rotating arm 2 through a screw. During specific implementation, other connection manners may also be adopted. In this embodiment, the electrical motor 4 is also used to drive the magnetically permeable rotating arm 2 and the high field magnets 1 on the magnetically permeable rotating arm 2 to rotate at a low frequency.

Besides the above embodiments, the present invention also has other implementation manners, which will not be listed herein. In the above four embodiments and the accompanying drawings, two high field magnets are symmetrically mounted on the magnetically permeable rotating arm 2, and mounting two high field magnets on the magnetically permeable rotating arm 2 is also a preferred implementation manner of the present invention. In addition, in the present invention, multiple high field magnets may also be mounted on the magnetically permeable rotating arm 2, as long as the high field magnets are symmetrical in pairs. In the present invention, preferably, two symmetrical high field magnets are adopted. In the present invention, preferably, the electrical motor 4 and the magnetically permeable rotating arm 2 are connected through the key 6, so that the structure is simple, easy to implement, and reliable. During specific implementation, the present invention is not limited to the above structure, other connection manners such as belt connection and gear connection may also be adopted, as long as the electrical motor 4 can be used to drive the high field magnets 1 to rotate at a low frequency.

Figure 6:
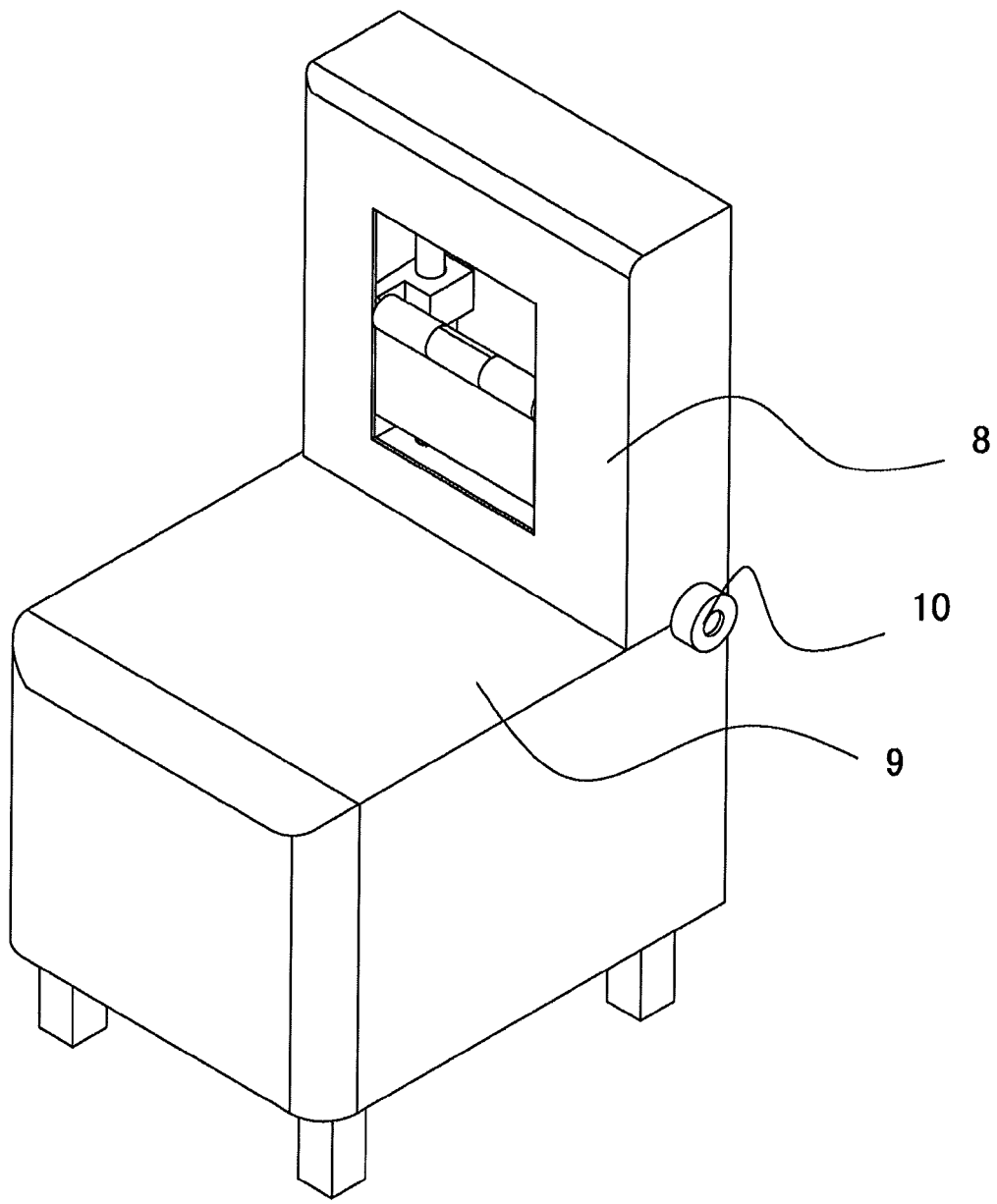
FIG. 6 is a three-dimensional schematic structural view of an application of the present invention.
Figure 7:
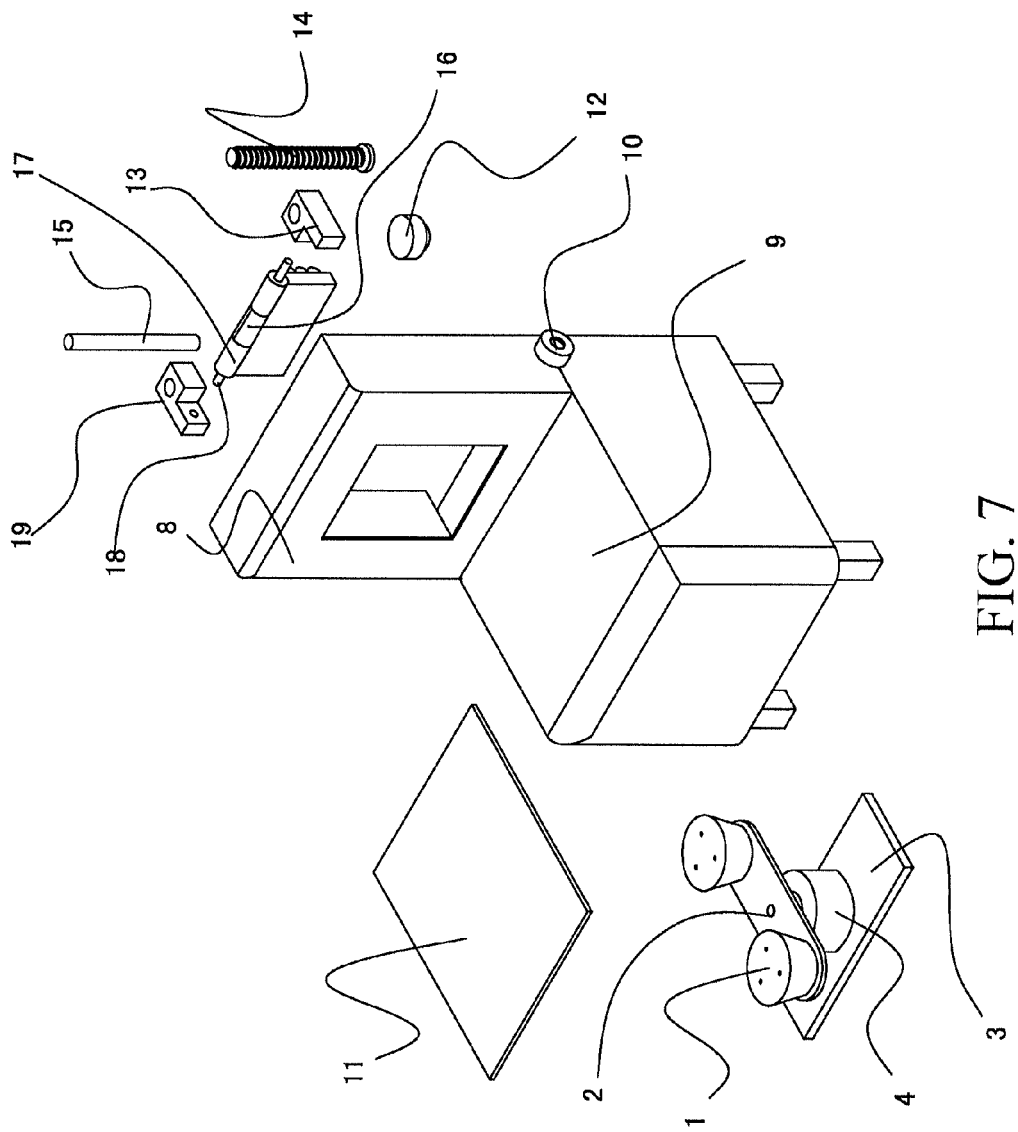
FIG. 7 is a schematic structural view of an exploded state of an application of the present invention.

Referring to FIG. 6 and FIG. 7, FIG. 6 and FIG. 7 show an application example of the present invention. The present invention can be applied to a magnetic therapy chair. A fixing plate 3 is fixedly mounted in a base 9 of the magnetic therapy chair. The rotating electrical motor 4 is fixedly mounted on the fixing plate 3. A bearing plate 11 is fixedly mounted in the base 9. The bearing plate 11 is disposed above the high field magnet 1, and is used for bearing the weight of a user, so as to prevent the user from affecting the rotation of the high field magnet 1 when the user is sitting on the chair. In this embodiment, the fixing plate 3 is made of an epoxy phenol aldehyde glass cloth laminated board (that is, the so-called bakelite board). The fixing plate 3 is made of a non-magnetically permeable material, and cannot be made of magnetically permeable materials such as iron, so that magnetic lines of force can penetrate the fixing plate 3 smoothly. Another set of magnetic therapy mechanism is installed in the magnetic therapy chair 8, including an up-down electrical motor 12 for enabling the magnet to move up and down, a longitudinal guide rod 15, and a lead screw 14, in which the up-down electrical motor 12 drives the lead screw 14 to rotate. In this embodiment, the up-down electrical motor 12 drives the lead screw 14 to rotate through a belt, and during specific implementation, other driving manners such as a gear may be adopted. The lead screw 14 is sleeved with a guide block 13, so that when the lead screw 14 rotates, the guide block 13 can move downward along the lead screw 14. In this embodiment, the simplest structure of the guide block 13 is provided, that is, an internal thread is formed in the guide block 13. In this embodiment, the lead screw 14 is disposed upright, and the longitudinal guide rod 15 is disposed parallel to the lead screw 14. In this embodiment, the longitudinal guide rod 15 is sleeved with a slide block 19. A traverse guide rod 18 capable of moving up and down is connected between the guide block 13 and the slide block 19. The traverse guide rod 18 is used as a rotating shaft and passes through a rolling magnet capable of moving up and down, so that the rolling magnet capable of moving up and down can rotate with the traverse guide rod as a rotating shaft. In this embodiment, a part of the rolling magnet capable of moving up and down is exposed outside the backrest 8. When the up-down electrical motor 12 drives the lead screw 14 to rotate through the belt, the guide block 13 drives the traverse guide rod 18 to move up and down in a reciprocating motion. The traverse guide rod 18 drives the rolling magnet capable of moving up and down to move up and down in a reciprocating motion. The rolling magnet capable of moving up and down slides and rotates on the back of the user to implement magnetic therapy. In this embodiment, the rolling magnet capable of moving up and down is cylindrical and includes three segments, in which two ends are respectively action magnets 17, and the middle portion is a guide magnet 16. The guide magnet 16 is cylindrical, and is formed by two semi-cylindrical magnets. Magnet poles of opposite surfaces of the two semi-cylindrical magnets are the same, so that a magnetizing direction thereof is perpendicular to the rotating shaft. The two action magnets 17 at the two ends are also cylindrical, and a magnetizing direction thereof is parallel to the rotating shaft. Magnetic poles of surfaces of the two action magnets 17 contacting the guide magnet 16 are the same, so that magnetic lines of force in the action magnets 17 are concentrated and emerge outward under the action of the guide magnet 16, thereby achieving the magnetic therapy effect. In this embodiment, an angle between the backrest 8 and the base 9 is adjustable, so that the user receives the magnetic therapy in the most comfortable posture.

When the present invention is applied, the electrical motor 4 drives the magnetically permeable rotating arm 2 to rotate with a low frequency. The high field magnets 1 on the magnetically permeable rotating arm 2 move in a circular motion along with the magnetically permeable rotating arm 2. Meanwhile, the external magnetic field is that magnetic lines of force of the high field magnets 1 emerge from one magnet and are retrieved by another magnet, and the internal magnetic field is that magnetic lines of force of one magnet enter another magnet through the magnetically permeable rotating arm 2. The high field magnet 1 in the present invention is in a shape of a cone, and the cross section is in a geometric shape without edges or corners, so as to reduce the magnetic lines of force emerging around the magnet to affect other electrical appliances. Meanwhile, a free surface edge (that is, a position at a bottom surface of the cone) of the high field magnet 1 is angular and has the strongest magnetic lines of force, so that the magnetic lines of force emerge with maximum intensity, thereby ensuring the intensity and the emerging height of the magnetic lines of force. Combined with the rolling magnet capable of moving up and down in the backrest 8, the high field magnet can perform effective magnetic therapy and health care on human body. The present invention can also be applied to a magnetic therapy bed or other magnetic therapy apparatuses.

What is the claimed is:

1. A method for implementing a low-frequency rotating constant high magnetic field, comprising:
    disposing at least one pair of high field magnets including a first high field magnet and a second high field magnet, and
    disposing a magnetically permeable rotating arm,
    wherein the first and second high field magnets are symmetrically mounted relative to a rotation axis, the first high field magnet having a first connecting surface, and the second high field magnet having a second connecting surface, both of the first and second connecting surfaces are fixedly mounted on a same surface of the magnetically permeable rotating arm,
    wherein the first high field magnet has a first free surface generally opposite to the first connecting surface, and the second high field magnet has a second free surface generally opposite to the second connecting surface, a magnetic pole of the first free surface is opposite to a magnetic pole of the second free surface,
    wherein an area of the first free surface is larger than an area of the first connecting surface, and an area of the second free surface is larger than an area of the second connecting surface,
    wherein a cross section of the first high field magnet is in a geometric shape without corners, and a cross section of the second high field magnet is in a geometric shape without corners,
    wherein a rotating apparatus drives the magnetically permeable rotating arm and the first and second high field magnets to rotate about the rotation axis, and
    wherein an area of a cross section of the first high field magnet decreases from the first free surface to the first connecting surface, and an area of a cross section of the second high field magnet decreases from the second free surface to the second connecting surface.

2. The method for implementing a low-frequency rotating constant high magnetic field according to claim 1, wherein the cross section of the first high field magnet is in a shape of a circle or an ellipse, and the cross section of the second high field magnet is in a shape of a circle or an ellipse.

3. The method for implementing a low-frequency rotating constant high magnetic field according to claim 2, wherein each of the first and second high field magnets is in a tapered or a cone shape.

4. The method for implementing a low-frequency rotating constant high magnetic field according to claim 1, wherein each of the first and second high field magnets is in a tapered shape with an ellipse-shaped cross section, in a cone shape with an ellipse-shaped cross section, or in a hemisphere shape with an ellipse-shaped cross section.

5. The method for implementing a low-frequency rotating constant high magnetic field according to claim 3, wherein each of the first and second high field magnets is in a tapered shape with a circle-shaped cross section, in a cone shape with a circle-shaped cross section, or in a hemisphere shape with a circle-shaped cross section.

6. The method for implementing a low-frequency rotating constant high magnetic field according to claim 1, further comprising: disposing a second pair of high field magnets including a third high field magnet and a fourth high field magnet.

7. The method for implementing a low-frequency rotating constant high magnetic field according to claim 1, wherein the magnetically permeable rotating arm is made of an iron plate with high magnetic permeability.

8. The method for implementing a low-frequency rotating constant high magnetic field according to claim 1, wherein the rotating apparatus is an electrical motor, a mounting hole is opened on a support plate, an electrical motor shaft is inserted in the mounting hole, and a key connection is adopted between the electrical motor shaft and the support plate.

* * * * *